United States Patent
Yang et al.

(10) Patent No.: US 7,927,414 B2
(45) Date of Patent: Apr. 19, 2011

(54) METHOD OF MANUFACTURING ACELLULAR MATRIX GLUE

(75) Inventors: Chunlin Yang, Belle Mead, NJ (US); Thomas Matalenas, Bound Brook, NJ (US); Raymond S. Shissias, Iselin, NJ (US); Kerstin Spychaj, Norderstedt (DE)

(73) Assignee: Ethicon, Inc., Somerville, NJ (US)

( * ) Notice: Subject to any disclaimer, the term of this patent is extended or adjusted under 35 U.S.C. 154(b) by 327 days.

(21) Appl. No.: 12/204,888

(22) Filed: Sep. 5, 2008

(65) Prior Publication Data

US 2010/0058952 A1    Mar. 11, 2010

(51) Int. Cl.
*C09J 189/00* (2006.01)
(52) U.S. Cl. .................. 106/124.4; 424/548; 424/551; 424/569; 424/572; 424/583; 606/214
(58) Field of Classification Search .............. 106/124.4; 424/548, 551, 569, 572, 583; 602/214
See application file for complete search history.

(56) References Cited

U.S. PATENT DOCUMENTS

| | | | | |
|---|---|---|---|---|
| 5,275,826 A * | 1/1994 | Badylak et al. | | 424/551 |
| 5,336,616 A | 8/1994 | Livesey et al. | | |
| 5,516,533 A * | 5/1996 | Badylak et al. | | 424/551 |
| 6,206,931 B1 * | 3/2001 | Cook et al. | | 623/23.75 |
| 6,264,992 B1 * | 7/2001 | Voytik-Harbin et al. | | 424/551 |
| 6,326,019 B1 | 12/2001 | Tseng | | |
| 6,638,312 B2 | 10/2003 | Plouhar et al. | | |
| 6,726,718 B1 * | 4/2004 | Carlyle et al. | | 623/2.42 |
| 7,160,333 B2 | 1/2007 | Plouhar et al. | | |
| 7,198,855 B2 * | 4/2007 | Liebmann-Vinson et al. | | 428/447 |
| 7,217,294 B2 * | 5/2007 | Kusanagi et al. | | 623/18.11 |
| 2002/0123805 A1 * | 9/2002 | Murray et al. | | 623/13.17 |
| 2003/0187515 A1 | 10/2003 | Hariri et al. | | |
| 2003/0225355 A1 * | 12/2003 | Butler | | 602/48 |
| 2004/0067582 A1 | 4/2004 | Wolfinbarger, Jr. et al. | | |
| 2006/0073592 A1 | 4/2006 | Sun et al. | | |
| 2006/0147433 A1 * | 7/2006 | Hiles | | 424/93.7 |
| 2007/0237973 A1 | 10/2007 | Purdy et al. | | |
| 2008/0057097 A1 * | 3/2008 | Benco et al. | | 424/423 |
| 2010/0028396 A1 * | 2/2010 | Ward et al. | | 424/405 |

FOREIGN PATENT DOCUMENTS

WO   WO 01/49827 A1   7/2001
WO   2007/050902 A1   5/2007

OTHER PUBLICATIONS

Kruse, F.E., et al. (2000)., "Cryoperserved Human Amniotic Membrane For Ocular Surface Reconstruction," *Graefe's Arch. Clin. Exp. Ophthalmol.*, 238:68-75.

* cited by examiner

*Primary Examiner* — David M Brunsman
(74) *Attorney, Agent, or Firm* — Emil Richard Skula

(57) ABSTRACT

An acellular matrix glue and a method of making is disclosed. Specifically, an acellular matrix glue that is useful in preparing a reinforced acellular matrix for medical applications including tissue engineering and hernia repair.

9 Claims, 2 Drawing Sheets

METHOD OF MANUFACTURING ACELLULAR MATRIX GLUE

This patent application is related to commonly-assigned patent application Ser. No. 12/204,855, filed on evendate herewith and entititled "Acellular Matrix Glue".

FIELD OF THE INVENTION

The present invention relates generally to the field of natural biomaterials, more specifically, to biocompatible glues, such as bioglue.

BACKGROUND OF THE INVENTION

Extracellular matrix (ECM) has been long recognized as an important structural component of connective tissues. ECM is generally described as a filamentous structure of glycoproteins and proteoglycans that is attached to the cell surface and provides cells with anchorage, traction for movement, and positional recognition. There is now considerable evidence that the ECM elaborated by cells creates microenvironments that these and other cells will respond to, by differentiating or maintaining their differentiated state. ECM provides a substrate for organization of cells which adhere to it. Tissue based ECM biomaterial and devices have been widely used for a variety of medical applications, such as heart valves, porcine small intestinal submucosa (SIS), human dermis and bovine pericardium. Allogenic or xenogenic connective tissues, such as skin, tendon, pericardium and SIS are decellularized (or devitalized) using known, conventional methods to provide a type of extracellular matrix called acellular matrix, which may also be referred to as decellularized matrix. During decellularization, the cells that lead to tissue rejection are removed while retaining the critical biochemical and structural components of the original tissue.

The use of acellular matrix for certain applications in medical devices is known in the art. One example is bioprosthetic devices for soft tissue attachment, reinforcement, or construction. The devices have a sheet of naturally occurring extracellular matrix and a sheet of synthetic mesh coupled to the naturally occurring extracellular matrix portion. The implants may be dried under vacuum pressure resulting in a physical cross-linking between the laminates of SIS and between the mesh and adjacent SIS laminates.

It is also known to use an acellular matrix with a reinforced biological tissue. The methods to marry or combine the biologic component and non-biological components include tissue around non-biologic component, non-biologic around tissue, or tissue embedded within or coating a knit, weave, braid or other textile of non-biologic component. The two components can be co-mingled or the separated components can be layered and rolled tightly around another. Compressive force may be added to the layered construct by including securing straps, similar to a belt and hoop design.

Known shortcomings and deficiencies of the conventional approaches to combine synthetic constructs with acellular matrix include delamination, poor handling properties, and cumbersome processing techniques. Therefore, there is a need for novel methods for combining an acellular matrix with a synthetic scaffold.

SUMMARY OF THE INVENTION

Accordingly, a novel acellular matrix glue and a novel method of making an acellular matrix glue are disclosed. Also disclosed is a novel reinforced acellular matrix.

The acellular matrix glue has an acellular matrix in an aqueous solution.

Another aspect of the present invention is a novel method of making the acellular matrix glue of the present invention. The method includes the steps of providing an acellular matrix. The acellular matrix is added to an aqueous solution to provide a mixture. The mixture is incubated in a sufficient temperature range for a sufficient time to effectively form an acellular matrix glue.

Yet another aspect of the present invention is a novel reinforced acellular matrix. The matrix has an acellular matrix layer, an acellular matrix glue layer, and a reinforcement layer. Wherein, the acellular matrix glue layer is the novel acellular matrix glue of the present invention.

A further aspect of the present invention is a method of performing a hernia repair using the novel acellular matrix of the present invention.

These and other aspects and advantages of the present invention will become more apparent from the following description and accompanying drawings.

DETAILED DESCRIPTION OF THE INVENTION

Figure 1:
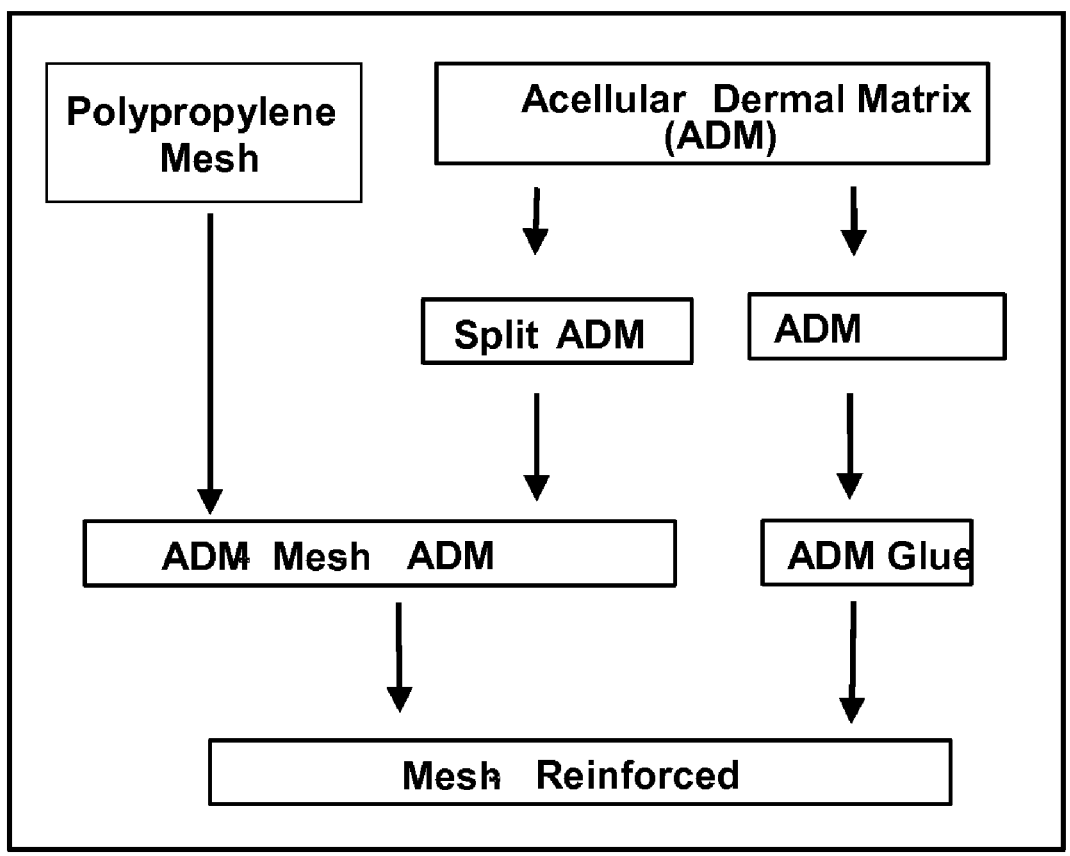
FIG. 1 is a diagram showing the steps used to prepare an acellular matrix glue of the present invention, and a reinforced acellular matrix of the present invention.

The acellular matrix glues of the present invention ares prepared by providing an acellular matrix, mixing the acellular matrix in an aqueous solution to form an acellular matrix mixture, then incubating the acellular matrix mixture for a sufficiently effective time at a sufficiently effective temperature to provide the acellular matrix glue.

Acellular matrix is defined herein as tissue that has been decellularized such that the nuclear and cellular components are removed from the structural extracellular matrix. Acellular matrix is prepared from tissue, including organs or isolated parts of organs. The tissue includes, but is not limited to heart valves, small intestine submucosa, dermis, amniotic membrane, bladder, omentum, pericardium, ligament, blood vessel, and the like. In one embodiment, the tissue includes, but is not limited to omentum and dermis. In another embodiment, the tissue is dermis. The tissue may be obtained from various mammalian sources including but not limited to human, goat, porcine, bovine, ovine, equine and the like. The tissue is decellularized by conventional techniques, including steps such as tissue preservation, decullarization, washing, decontamination and storage.

The decellularization step commonly involves removal of the cellular components by extraction using salt solutions containing detergents and digestion by endonuclease.

The acellular matrix is then transferred into an aqueous solution. In one embodiment, the acellular matrix is processed into smaller pieces prior to transferring to the aqueous solution. The acellular matrix may be processed into smaller pieces by conventional methods such as cutting with scissors, a blade, or a knife; milling into a powder, such as ball milling and cryogenic milling; and jet milling. Processing of the acellular matrix into smaller pieces, such as into a powder, provides more surface area and therefore enables faster dissolution in to the aqueous solution. In one embodiment, the acellular matrix is processed into a powder by cryogenic milling prior to adding to the aqueous solution.

Aqueous solutions useful in the practice of the present invention include, but are not limited to water, physiological buffer, and saline. Physiological buffer includes, but is not limited to buffered saline, such as phosphate buffered saline (PBS); Hank's balanced salts solution, Tris buffered saline, and Hepes buffered saline. In one embodiment, the aqueous solution is water.

In one embodiment, the aqueous solution optionally includes a sufficiently effective amount of a plasticizer. Plasticizers include but are not limited to glycerol, propylene glycol, polyethylene glycol. In one embodiment, the plasticizer is glycerol.

The acellular matrix glue is prepared, for example by providing an acellular matrix, such as acellular dermal matrix. The acellular dermal matrix is then optionally processed into a powder by cryogenic milling. The acellular matrix powder has a particle size of less than about 2 mm. About 1.0 g of acellular matrix powder is mixed into 10 ml of an aqueous solution, such as water or phosphate buffered saline (PBS) to form an acelluar matrix mixture. The acellular matrix is present in amount of typically about 2% to about 30% by weight, preferably about 5% to about 20% by weight of the aqueous solution. In another embodiment, the acellular matrix is present in amount of about 10% by weight of the aqueous solution. The acellular matrix mixture is then incubated at a sufficiently effective temperature and time, typically about 70° C. to about 100° C. for about 10 minutes to about 48 hours, preferably from about 80° C. to about 90° C., and typically for about 1 hour to about 5 hours. Higher temperature can also be used under higher pressure, for example 120° C. at 2 atmosphere pressure. The acellular matrix glue is allowed to cool to approximately 37° C. for immediate use or allowed to cool to room temperature or below until ready to use.

In another embodiment, a sufficiently effective amount of a plasticizer such as, glycerol may be optionally added to increase the flexibility and wetting property of the glue. The plasticizer may be added in an amount based on the nature of the plasticizer. In the case of glycerol, the amount of glycerol added to the acellular matrix glue is typically about 0.5% to about 10% by weight of the aqueous glue. The plasticizer may be added and mixed uniformly into the aqueous glue either prior to or after allowing the glue to cool. Preferably, the glycerol is added prior to allowing the glue to cool for ease of mixing and uniform distribution in the glue.

The acellular matrix glue as described herein is useful for preparing reinforced acellular matrix for tissue repair and engineering. The reinforced acellular matrix of the present invention utilizing the acellular matrix glue of the present invention consists of an acellular matrix layer, a reinforcement layer, and ane acellular matrix glue layer. Although not preferred, the acellular matrix glues of the present invention may also be used as a tissue glue or sealant if those skilled in the art were willing to accept the disadvantages, if any, attendant therewith.

The acellular matrix layer is prepared from acellular matrix. Acellular matrix is prepared from tissue, including organs or isolated parts of organs. The tissue includes, but is not limited to heart valves, small intestine submucosa, dermis, amniotic membrane, bladder, omentum, pericardium, ligament, blood vessel, and the like. In one embodiment, the tissue includes, but is not limited to omentum and dermis. In another embodiment, the tissue is dermis. The tissue may be obtained from various mammalian sources including but not limited to human, goat, porcine, bovine, ovine, equine and the like. As described above, the tissue is decellularized using conventional processes and techniques to provide the acellular matrix. The acellular matrix layer is obtained by splitting the acellular matrix into thin sheets having a thickness of typically from about 50 microns to about 200 microns. The acelluar matrix is split by conventional techniques such as, using a cowhide splitter.

The reinforcement layer is preferably a textile or similar or equivalent material including but not limited to woven, knitted, warped knitted (i.e., lace-like), non-woven, and braided structures. Although not preferred, the reinforcement layer may be a sheet of material that is not a textile, for example, such as a polymer sheet. In one embodiment the reinforcement layer is a woven textile, such as a mesh. In the above textiles and materials, the mechanical properties can be adjusted by changing the density or texture of the textile or material. The fibers used to make the textile can be, for example monofilaments, yarns, threads, braids, or bundles of fibers. The materials such as polymer sheets may have holes formed or drilled therein, and may be optionally porous. The fibers and materials such as sheets can be made of biocompatible, bioabsorbable materials, including, but not limited to polylactic acid (PLA)(including polylactide), polyglycolic acid (PGA) (including polyglycolide), polycaprolactone (PCL), polydioxanone (PDO), and polytrimethylene carbonate (PTMC). The fibers may also be made of biocompatible, non-absorbable polymers including but not limited to polyolefins, polycarbonates, polyvinylchlorides, styrenes, including acrylonitrile butadiene styrenes, nylons, acrylics, thermoplastic urethanes, thermoplastic elastomers, thermoset plastics, polyamides, polyesters, moldable silicon, polyethylene terephthalate, polyvinyl alcohol (PVA), and copolymers or blends thereof. Suitable polyolefins include but are not limited to polyethylene, polypropylene, and copolymers and thereof. In one embodiment, the fibers that comprise the textile are formed of polypropylene.

In one embodiment, the reinforced acellular matrix is prepared by providing a reinforcement layer, an acellular matrix layer, and an acellular matrix glue. The acellular matrix glue should be heated to a sufficiently effective temperature to denature the collagen components of the acellular matrix, typically from about 50° C. to about 90° C. and then allow to cool to a desired temperature, typically from about 30° C. to about 50° C., preferably to about 37° C. prior to use. The acellular matrix glue is then disposed in a sufficient amount between the acellular matrix layer and the reinforcement layer to effectively bind the matrix layers and the reinforcement layer and allowed to dry in a conventional manner to form the reinforced acellular matrix. For example, the matrix may be made by providing a reinforcement layer having a top and a bottom side, placing a layer of acellular matrix glue on the topside of the reinforcement layer, and then placing the acellular matrix on the glue layer thereby gluing the reinforcement layer and the acellular matrix layer together. Alternatively, the matrix may be made by providing the acellular matrix layer, placing a layer of acellular matrix glue on the acellular matrix layer, and then placing the reinforcement layer on the glue layer thereby gluing the reinforcement layer and the acellular matrix layer together. A multi-layer reinforced acellular matrix may also be provided by continuing to alternate the reinforcement layer, acellular matrix glue layer and acellular matrix layer or by varying the positions of the layered materials in the structure. The acellular matrix glue and the acellular matrix layer may have been prepared from either the same tissue type or from different tissue types as described herein above. In one embodiment, the acellular matrix layer and the acellular matrix glue layer are from the same tissue type.

Optionally, the reinforced acellular matrix can be stabilized by cross-linking the acellular matrix glue layer and the acellular matrix layer using conventional methods, such as using formadehyde vapor, glutaraldehyde, 1-ethyl-3-(3-dimethylaminopropyl) carbodiimide hydrochloride (EDC) or oxidized polysaccharides. Polysaccharides include, but are not limited to hyaluronic acid, chondroitin sulfate, dermatan sulfate, keratan sulfate, heparan, heparan sulfate, dextran, dextran sulfate, alginate, and other long chain polysaccharides. In one embodiment, the reinforced acellular matrix is stabilized by EDC cross linking, including 1% EDC in a solution containing alcohol, such as ethanol, isopropanol, propanol, preferably at a concentration between about 40% to about 70%.

In one embodiment, one or more bioactive agents may optionally be incorporated within and/or applied to the reinforced acellular matrix. In one embodiment the bioactive agent is incorporated within, or coated on, the reinforcement component. In another embodiment, the bioactive agent is incorporated into the acellular matrix glue. In yet another embodiment, the bioactive agent is incorporated into the acellular matrix.

Suitable bioactive agents include, but are not limited to agents that prevent infection (e.g., antimicrobial agents and antibiotics), agents that reduce inflammation (e.g., anti-inflammatory agents), agents that prevent or minimize adhesion formation, such as oxidized regenerated cellulose (e.g., INTERCEED and SURGICEL, available from Ethicon, Inc.) and hyaluronic acid, and agents that suppress the immune system (e.g., immunosuppressants) heterologous or autologous growth factors, proteins (including matrix proteins), peptides, antibodies, enzymes, platelets, platelet rich plasma, glycoproteins, hormones, cytokines, glycosaminoglycans, nucleic acids, analgesics, viruses, virus particles, and cell types, chemotactic agents, antibiotics, and steroidal and nonsteroidal analgesics.

A viable tissue can also be included in the reinforced acellular matrix of the present invention. The source can vary and the tissue can have a variety of configurations, however, in one embodiment the tissue is optionally in the form of finely minced or divided tissue fragments or pieces, which may enhance the effectiveness of tissue re-growth and encourage a healing response, e.g., cartilage. In another embodiment, the viable tissue can optionally be in the form of a tissue slice or strip harvested from healthy tissue that contains viable cells capable of tissue regeneration and/or remodeling.

The reinforced acellular matrix can also have viable cells incorporated therein. Suitable cell types include, but are not limited to, osteocytes, osteoblasts, osteoclasts, fibroblasts, stem cells, pluripotent cells, chondrocyte progenitors, chondrocytes, endothelial cells, macrophages, leukocytes, adipocytes, monocytes, plasma cells, mast cells, umbilical cord cells, stromal cells, mesenchymal stem cells, epithelial cells, myoblasts, tenocytes, ligament fibroblasts, neurons, bone marrow cells, synoviocytes, embryonic stem cells; precursor cells derived from adipose tissue; peripheral blood progenitor cells; stem cells isolated from adult tissue; genetically transformed cells; a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of precursor cells isolated from adult tissue and other cells; a combination of peripheral blood progenitor cells and other cells; a combination of stem cells isolated from adult tissue and other cells; and a combination of genetically transformed cells and other cells.

The reinforced acellular matrix of the present invention can also be used in gene therapy techniques in which nucleic acids, viruses, or virus particles deliver a gene of interest, which encodes at least one gene product of interest, to specific cells or cell types. Accordingly, the bioactive agent can be a nucleic acid (e.g., DNA, RNA, or an oligonucleotide), a virus, a virus particle, or a non-viral vector. The viruses and virus particles may be, or may be derived from, DNA or RNA viruses. The gene product of interest is preferably selected from the group consisting of proteins, polypeptides, interference ribonucleic acids (iRNA) and combinations thereof.

Once sufficiently effective amounts of the applicable nucleic acids and/or viral agents (i.e., viruses or viral particles) are incorporated into the reinforced acellular matrix, the device can then be implanted into a particular site to elicit a desired type of biological response. The nucleic acid or viral agent can then be taken up by the cells and any proteins that they encode can be produced locally by the cells. In one embodiment, the nucleic acid or viral agent can be taken up by the cells within the tissue fragment of the minced tissue suspension, or, in an alternative embodiment, the nucleic acid or viral agent can be taken up by the cells in the tissue surrounding the site of the injured tissue. One skilled in the art will recognize that the protein produced can be a protein of the type noted above, or a similar protein that facilitates an enhanced capacity of the tissue to heal an injury or a disease, combat an infection, or reduce an inflammatory response. Nucleic acids can also be used to block the expression of unwanted gene product that may impact negatively on a tissue repair process or other normal biological processes. DNA, RNA and viral agents are conventionally used to accomplish such an expression blocking function, which is also known as gene expression knock out.

One skilled in the art will appreciate that the identity of the bioactive agent may be determined by a surgeon, health care professional, or other life sciences professional, based on principles of medical science and the applicable treatment objectives. It is also understood that the bioactive agent can be incorporated within the reinforced acellular matrix before, during, or after manufacture, or before, during, or after the surgical placement of the reinforced acellular matrix.

The reinforced acellular matrices of the present invention may be used in the following surgical procedures where tissue reinforcement is desired, including but not limited to abdominal surgery, such as hernia repair and pelvic floor repair; cosmetic surgery, such as breast lifting and facial lifting, and other tissue repair surgery, such as rotator cuff repair. The acellular matrices are mounted to the tissue using conventional tissue attachment devices including glues, sutures, staples, tacks and the like.

The following examples are illustrative of the principles and practice of this invention, although not limited thereto. Numerous additional embodiments within the scope and spirit of the invention will become apparent to those skilled in the art once having the benefit of this disclosure.

EXAMPLE 1

Process For Formulating Acellular Matrix Glue

An acellular porcine dermal matrix sold under the tradename DermMatrix (by Advanced UroScience, St. Paul, Minn.) was milled into fine powder using a 6800 Freezer Mill (SPEX CertiPrep, Metuchen, N.J.). 1.0 gram of acellular dermal matrix powder was added into 10 ml of aqueous solution containing 7% glycerol and 1.3% acetic acid in a polypropylene tube. The tube was placed into an 80° C. water bath with magnetic stirring. After 3 hours of incubation at 80° C. the glue became opaque. The glue is removed from the water bath and allowed to cool down to 37° C. before use. The process is illustrated in FIG. 1.

EXAMPLE 2

Preparation Of Thin Layers Of Acellular Porcine Dermal Matrix

An acellular porcine dermal matrix, sold under the tradename DermMatrix (by Advanced UroScience, St. Paul, Minn.) was split into thin layers using a leather splitting machine (performed by Columbia Organ Leather, Columbia, Pa.) for prototype formulation. The acellular porcine dermal matrix was soaked in IPA for 24 hours before splitting. An 8 cm×8 cm square of acellular porcine dermal matrix was fed into the splitting machine and split to a final thickness range of 0.19 mm to 0.10 mm. After splitting the acellular porcine dermal matrix sheets were stored in IPA for further processing until ready to use. This process was repeated for all acellular porcine dermal matrix samples.

EXAMPLE 3

Preparation Of Reinforced Acellular Porcine Dermal Matrix

The process for preparing mesh reinforced acellular dermal matrix is shown in FIG. 1. The split acellular dermal matrix samples prepared in Example 2 were washed with deionized water and then lyophilized at 20° C. A light weight polypropylene mesh was prepared by incubating Ultrapro mesh (Ethicon Inc. Somerville, N.J.) in deionized water at 50° C. for 10 days to remove its absorbable component. The light polypropylene mesh was placed between two layers of 3×5 cm split acellular dermal matrix and was glued together with 3 ml of the acellular matrix glue prepared in Example 1 kept at 37° C. The whole construct was cooled down to room temperature and air dried in a cell culture hood.

EXAMPLE 4

Stabilization Of Mesh-Reinforced Acellular Porcine Dermal Matrix

A reinforced acellular dermal matrix prepared as described in Example 3 was washed with 100 ml of ethanolic phosphate buffered saline (PBS) solution (40% ethanol) for 30 minutes. The washed reinforced acellular dermal matrix was then transferred into 50 ml of 10 mg/ml 1-ethyl-3-(3-dimethylaminopropyl) carbodiimide hydrochloride (EDC) in (prepared fresh) ethanolic PBS. After 4 hour incubation at room temperature, the crosslinked reinforced acellular matrix was washed twice with 6% glycerol (w/w) in water. The crosslinked reinforced acellular matrix was air dried.

EXAMPLE 5

Evaluation Of Mesh-Reinforced Acellular Dermal Matrix By Sem

Figure 2:
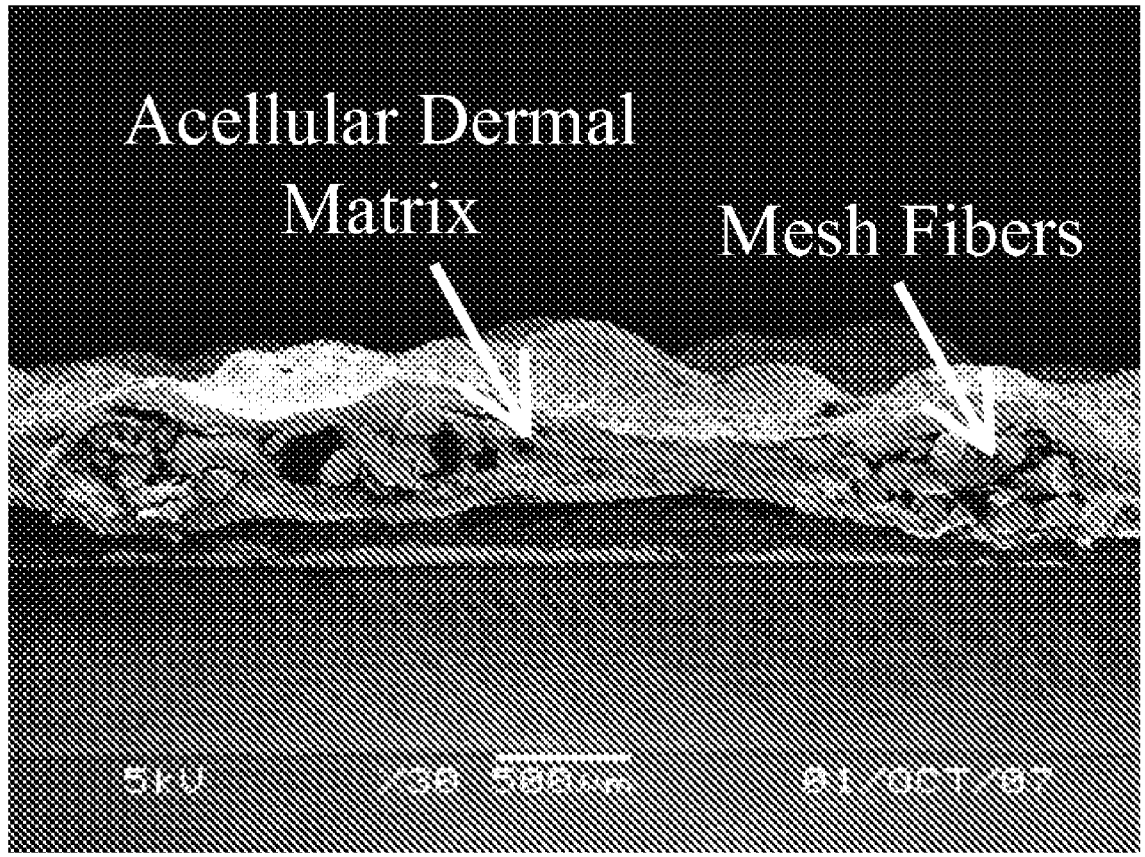
FIG. 2 is an SEM image of mesh-reinforced acellular dermal matrix of the present invention.

The samples prepared in Example 4 were mounted on a microscope stud and coated with a thin layer of gold using the EMS 550 sputter coater (Electron Microscopy Sciences, Hatfield, Pa.). SEM analysis was performed using the JEOL JSM-5900LV SEM (JEOL, Tokyo, Japan). The surfaces and cross-sectional areas were examined for each sample. The SEM images (See FIG. 2) showed that the mesh is embedded in the center of two thin layers of acellular dermal matrix.

EXAMPLE 6

Hernia Repair Animal Model

Using a porcine model, the subjects are anesthetized and prepped for surgery in a conventional manner. Midline incisions were made above/cranial and/or below/caudal to the umbilicus: A ventral midline incision is made through the skin and subcutaneous tissue to expose the abdominal wall fascia in the midline/linea alba. Two median defects cranial and caudal to the umbilicus approximately 3 cm in length are made in the linea alba exposing pre-peritoneal fat tissue and peritoneum. The mesh-reinforced acellular matrix is trimmed to appropriate size, deployed flat on the abdominal fascia with suture fixation PROLENE sutures size # 3-0 (Ethicon, Inc., Somerville, N.J.).

Subcutaneous tissue and skin are closed with single Monocryl sutures size USP 3-0. Additionally, the skin is glued with a a topical skin adhesive to prevent early wound contamination.

EXAMPLE 7

Open Human Hernia Repair With Reinforced Acellular Matrix

A human patient is prepared in a conventional manner for an open hernia repair procedure. General anesthesia is given in a conventional manner, optionally, the patient may have conventional local or regional anesthesia, depending on the location of the hernia and complexity of the repair. A catheter is optionally inserted into the bladder to remove urine and decompress the bladder.

An incision is made just large enough to remove fat and scar tissue from the abdominal wall near the hernia. The outside edges of the weakened hernial area are defined and excess tissue removed from within the area. Reinforced acellular matrix of the present invention is then applied so that it overlaps the weakened area by several inches (centimeters) in all directions and fixed in place with non-absorbable sutures. The abdominal wall is then approximated and closed with non-absorbable sutures. The sutures are tied down and knotted.

Compared to the conventional approaches to combine synthetic constructs with acellular matrix, the synthetic constructs and the acellular matrix in the constructs disclosed in the present invention are well integrated to avoid delamination. As a result, the constructs is flexible. The acellular matrix glue provides a delivery medium for incorporating bioactives into the composite constructs.

Although this invention has been shown and described with respect to detailed embodiments thereof, it will be understood by those skilled in the art that various changes in form and detail thereof may be made without departing from the spirit and scope of the claimed invention.

We claim:
1. A method of making an acellular matrix glue comprising the steps of:
providing an acellular matrix; adding the acellular matrix to an aqueous solution to provide a mixture; and, incu- bating the mixture for a sufficiently effective time at a sufficiently effective temperature to form an acellular matrix glue.

2. The method of claim 1, wherein the temperature is in the range of about 70° C. to about 100° C.

3. The method of claim 1, wherein the time is in the range of about 10 minutes to about 48 hours.

4. The method of claim 1, comprising the additional step of allowing the acellular matrix glue to cool to about 37° prior to use.

5. The method of claim 1, wherein 1 wherein the acellular matrix comprises decellularized tissue obtained from a mammalian source selected from the group consisting of human, goat, porcine, bovine, ovine, and equine.

6. The method of claim 5, wherein the decellularized tissue is selected from the group consisting of heart valves, small intestine submucosa, dermis, amniotic membrane, bladder, omentum, pericardium, ligament, and blood vessel.

7. The method of claim 1, wherein the aqueous solution is selected from the group consisting of water, physiological buffer, and saline.

8. The method of claim 1, wherein the acellular matrix glue additionally comprises a plasticizer selected from the group consisting of glycerol, propylene glycol, and polyethylene glycol.

9. The method of claim 1 wherein the acellular matrix glue comprises about 2 (w/v) % of acellular matrix and about 30 (w/v) % of aqueous solution.

\* \* \* \* \*